United States Patent [19]

Gay et al.

[11] 4,353,920
[45] Oct. 12, 1982

[54] USE OF SELECTED 3-TRIHALOMETHYL-5-UREIDO-1,2,4-OXADIAZOLES AND -1,2,4-THIADIAZOLES AS AGRICULTURAL VIRICIDES

[75] Inventors: Walter A. Gay, Cheshire; Elizabeth A. Twohig, Seymore, both of Conn.

[73] Assignee: Olin Corporation, New Haven, Conn.

[21] Appl. No.: 334,483

[22] Filed: Dec. 24, 1981

Related U.S. Application Data

[62] Division of Ser. No. 181,039, Aug. 25, 1980.

[51] Int. Cl.³ .................. A01N 47/36; C07D 271/06; C07D 285/08
[52] U.S. Cl. .................. 424/270; 424/272; 548/128; 548/133
[58] Field of Search ............. 424/270, 272; 548/133, 548/128

[56] References Cited

U.S. PATENT DOCUMENTS

| | | | |
|---|---|---|---|
| 2,399,599 | 4/1946 | Kaiser | 548/133 |
| 3,673,203 | 6/1972 | Miller | 548/128 |
| 3,686,198 | 8/1972 | Metzger et al. | 548/128 |
| 3,822,280 | 7/1974 | Moser et al. | 548/128 |
| 3,884,929 | 5/1975 | Smith | 548/128 |
| 3,917,478 | 11/1975 | Moser et al. | 71/90 |
| 4,224,449 | 9/1980 | Tobin et al. | 548/128 |

*Primary Examiner*—Alton D. Rollins
*Attorney, Agent, or Firm*—William A. Simons; Thomas P. O'Day

[57] ABSTRACT

Disclosed are selected 3-trihalomethyl-5-ureido-1,2,4-oxadiazole and -1,2,4-thiadiazole compounds of the formula:

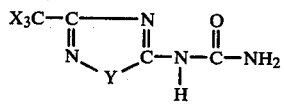

wherein X is either Cl or F and Y is either O or S. These compounds are shown to be effective against agricultural viruses.

5 Claims, No Drawings

USE OF SELECTED 3-TRIHALOMETHYL-5-UREIDO-1,2,4-OXADIAZOLES AND -1,2,4-THIADIAZOLES AS AGRICULTURAL VIRICIDES

This is a division of application Ser. No. 181,039, filed Aug. 25, 1980.

BACKGROUND OF THE INVENTION

1. Field of the Invention

This invention relates to selected 3-trihalomethyl-5-ureido-1,2,4-oxadiazole and -1,2,4-thiadiazole compounds and their use as agricultural viricides.

2. Description of the Prior Art

Various 3,5-disubstituted-1,2,4-oxadiazole and -1,2,4-thiadiazole compounds have been known to possess different types of pesticidal activity such as fungicidal, herbicidal, insecticidal, nematocidal and the like. For example, U.S. Pat. Nos. 3,673,203; 3,686,198; 3,822,280; and 3,917,478, which respectively issued to Miller on June 27, 1972; Metzger et al on Aug. 22, 1972, Moser et al on July 2, 1974; and Moser et al on Nov. 4, 1975, disclose various 1,2,4-oxadiazoles and 1,2,4-thiadiazoles which have ureido-substituents in the 5-position of these types of ring compounds. These disclosed 5-ureido compounds differ from the present invention because they either do not have 3-position substituents selected from trichloromethyl or trifluoromethyl (i.e., Miller or Metzger et al) or do not have an unsubstituted urea substituent in the 5-position (i.e., Metzger et al and the two Moser et al patents). Furthermore, none of these four references suggest that the compounds disclosed by them would be useful as agricultural viricides.

BRIEF SUMMARY OF THE INVENTION

The present invention is directed to, as compositions of matter, selected 3-trihalomethyl-5-ureido-1,2,4-oxadiazole and thiadiazole compounds of the formula (I):

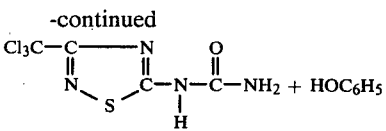

wherein X is either Cl or F and Y is either O or S. The present invention is also directed toward the use of these compounds as agricultural viricides.

DETAILED DESCRIPTION

The 3-trihalomethyl-5-ureido compounds of the present invention may be prepared by reacting the corresponding 3-trihalomethyl-5-phenylcarbamyl-1,2,4-oxadiazole or -1,2,4-thiadiazole compounds with ammonia in a suitable solvent, such as ethanol. This general reaction is illustrated by the following Equation (A) wherein 3-trichloromethyl-5-phenylcarbamyl-1,2,4-thiadiazole is reacted with ammonia:

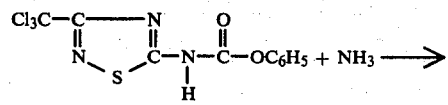

-continued
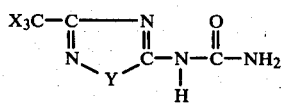

Suitable 3-trihalomethyl-5-phenylcarbamyl-1,2,4-oxadiazole and 1,2,4-thiadiazole compounds which can be used as precursors for the compounds of the present invention include, besides, 3-trichloromethyl-5-phenylcarbamate-1,2,4-thiadiazole, mentioned above, the following:

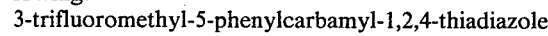
3-trifluoromethyl-5-phenylcarbamyl-1,2,4-thiadiazole
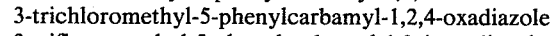
3-trichloromethyl-5-phenylcarbamyl-1,2,4-oxadiazole
3-trifluoromethyl-5-phenylcarbamyl-1,2,4-oxadiazole These 3-trihalomethyl-5-phenylcarbamate precursors are well known and are described in U.S. Pat. Nos. 3,822,280 and 3,917,478.

The ammonia reactant may be used neat either in gas or liquid form or dissolved in a suitable solvent. The latter is preferred since unpressurized reaction vessels may be used.

Any conventional reaction conditions designed to produce the 5-ureido compounds may be employed in the synthesis of the present compounds and the present invention is not intended to be limited to any particular reaction conditions. Advantageously and preferably, the reactions are performed with a large molar excess of ammonia to the particular 3-trihalomethyl-5-phenylcarbamyl precursor in the presence of a suitable inert solvent. A preferred class of solvents is alcohols. A preferred alcohol is ethanol. However, the use of a solvent is only desirable, but not necessary. The reaction temperature and time will both depend upon many factors including the specific reactants used. In most situations, reaction temperatures can advantageously be from about $-80°$ C. to $100°$ C. and reaction times from 1 hour to 100 hours or even more may be preferred. The product may be recovered from the reaction mixture by any conventional means, for example, filtration, extraction, slurrying with solvent, recrystallization or the like.

It should be noted that while the reaction illustrated by Equation (A) is a preferred method for preparing the compounds of the present invention, other synthetic methods may also be employed.

Also, in accordance with the present invention, it has been found that the compounds of Formula I, above, may be utilized as effective agricultural viricides. In practicing the process of the present invention, viruses are contacted with a viricidally effective amount of one or more of these compounds. "Agricultural viruses" are plant viruses which either cause mottling or spotting of leaves or cause yellowing, leaf curling, dwarfing or excessive branching. Generally, plant viruses are spread by contact with propagative plant materials, equipment or insects and also through infected seeds. It is to be understood that the term "viricidally effective amount" as used in the specification and claims herein is intended to include any amount that will kill or control said agricultural viruses when either employed by itself (i.e., in full concentration) or in sufficient concentrations with a carrier or other substance. Of course, this amount may be constantly changing because of the possible variations in many parameters. Some of these may include: the number and type of viruses to be controlled or killed; the type of media to which the present compound can be applied (e.g., soil, seed, seedling, or fully grown plant); degree of effectiveness required; and type of carrier, if any. Generally speaking applications of an aqueous spray containing at least about 5 parts per million, more preferably in the range of about 30 to 300 parts per million, of the chemical of the present invention may give satisfactory virus control.

This step of contacting may be accomplished by applying this compound to the viruses themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other viricides, fungicides, herbicides, insecticides and the like.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to about 15% by weight of the active compound with a finely divided inert diluent such as walnut flour, diatomaceous earth, fullers earth, attaclay, talc or kaolin. Dust concentrates are made in similar fashion except that about 16% to about 75% by weight of active compound is usually ground together with the diluent. In practice, dust concentrates are then generally admixed at the site of use with more inert diluent before it is applied to the plant foliage or soil which are to be protected from virus attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic or aromatic hydrocarbon or their derivatives. It is preferred that the solvent be odorless and moreover, be inert to the active compound.

It should be clearly understood that the viricide formulations, the ingredients which may make up such formulations other than the active compound, the dosages of these ingredients, and means of applying these formulations may include all known and conventional substances, amounts and means, respectively, that are suitable for obtaining the desired viricidal result. And, therefore, such process parameters are not critical to the present invention.

The viricides of the present invention may be effective for the control of the broad class of agricultural viruses. Specific illustrations of agricultural viruses wherein viricidal activity has been shown includes southern bean mosaic virus and tobacco mosaic virus.

The following examples further illustrate the present invention. All parts and percentages employed therein are by weight unless otherwise indicated. Yields given are percent molar yields.

EXAMPLE 1

A solution of 68.0 g (0.2 mole) 5-phenylcarbamyl-3-trichloromethyl-1,2,4-thiadiazole in 1000 ml ethanol was reacted at room temperature with 400 ml ammonia for 20 hours. The excess ammonia was allowed to vent through a condenser attached to the single neck glass reaction vessel. The reaction mixture was then refluxed for 6 hours and concentrated under vacuo. The crude product was dissolved in 250 ml methyl ethyl ketone, filtered and again concentrated under vacuo. After thorough washing with boiling benzene and petroleum ether, 40.0 g of analytically pure 3-trichloromethyl-5-ureido-1,2,4-thiadiazole with m.p. 205° C. was obtained in 77% yield.

| | C | H | N | Cl |
|---|---|---|---|---|
| Calculated | 18.37 | 1.16 | 21.42 | 40.67 |
| Found | 18.43 | 1.21 | 21.48 | 40.46 |

EXAMPLE 2

A solution of 14.5 g (0.05 mole) of 5-phenylcarbamyl-3-trifluoromethyl-1,2,4-thiadiazole in 500 ml ethanol was reacted at room temperature with 200 ml ammonia for 20 hours. The excess ammonia was allowed to vent through a condenser attached to the single neck glass reaction vessel. The reaction mixture was then refluxed for 4 hours and concentrated under vacuo. After recrystallization from acetonitrile, 8.6 g of analytically pure 3-trifluoromethyl-5-ureido-1,2,4-thiadiazole with m.p. 251° C. was obtained in 86% yield.

| | C | H | N | S |
|---|---|---|---|---|
| Calculated | 22.65 | 1.43 | 26.41 | 15.11 |
| Found | 22.66 | 1.51 | 26.18 | 14.97 |

EXAMPLE 3

A solution of 4.0 g (0.01 mole) 5-phenylcarbamyl-3-trichloromethyl-1,2,4-oxadiazole in 300 ml ethanol was reacted at room temperature with 150 ml ammonia for 3.5 days. The excess ammonia was allowed to vent through a condenser attached to the single neck glass reaction vessel. The reaction mixture was then concentrated under vacuo. After recrystallization from acetonitrile, 2.1 g of analytically pure 3-trichloromethyl-5- ureido-1,2,4-oxadiazole with m.p. 229° C. was obtained in 86% yield.

|  | C | H | N | Cl |
|---|---|---|---|---|
| Calculated | 19.57 | 1.23 | 22.83 | 43.33 |
| Found | 19.38 | 1.42 | 22.56 | 43.07 |

EXAMPLE 4

VIRICIDE SCREEN

A uniform aqueous dispersion of the compound of Example 1 was prepared by dissolving it in a solution of acetone containing the surfactant TRITON X-155 (concentration 500 ppm). Next, this solution was diluted with water (1:9) to obtain a stock solution of 10% by volume acetone and 90% by volume water (50 ppm TRITON X-155) and the test chemical contained therein. The solution was then sprayed onto the leaves of pinto bean plants which had been infected with a viral stock of southern bean mosaic virus. After 7 days at 75° F. under fluorescent light, the number of lesions on the treated plants and inoculated controls are counted and the precent reduction in lesions calculated by subtracting the mean number on the treated plants from the controls and dividing by the number on the controls. It was found that at a concentration of 260 ppm active ingredient the percent reduction of lesions was 90% and at 130 ppm, 80%.

What is claimed is:

1. The method of controlling agricultural viruses which comprises contacting said viruses with a viricidally effective amount of a compound of the formula:

$$X_3C-C=N, Y, C-N(H)-C(=O)-NH_2$$ (with ring N=C)

wherein X is either Cl or F and Y is either S or O.

2. The method of claim 1 wherein said compound has the formula:

$$Cl_3C-C=N, S, C-N(H)-C(=O)-NH_2$$

3. The method of claim 1 wherein said compound has the formula:

$$F_3C-C=N, S, C-N(H)-C(=O)-NH_2$$

4. The method of claim 1 wherein said compound has the formula:

$$Cl_3C-C=N, O, C-N(H)-C(=O)-NH_2$$

5. The method of claim 1 wherein said compound has the formula:

$$F_3C-C=N, O, C-N(H)-C(=O)-NH_2$$

* * * * *